(12) United States Patent
Hamada et al.

(10) Patent No.: US 7,998,595 B2
(45) Date of Patent: Aug. 16, 2011

(54) ORGANIC ELECTROLUMINESCENT DEVICE, LUMINESCENT MATERIAL AND ORGANIC COMPOUND

(75) Inventors: Yuji Hamada, Nara (JP); Noriyuki Matsusue, Hirakata (JP)

(73) Assignee: Sanyo Electric Co., Ltd., Osaka (JP)

( * ) Notice: Subject to any disclaimer, the term of this patent is extended or adjusted under 35 U.S.C. 154(b) by 1237 days.

(21) Appl. No.: 10/467,856

(22) PCT Filed: Feb. 12, 2002

(86) PCT No.: PCT/JP02/01162
§ 371 (c)(1),
(2), (4) Date: Feb. 19, 2004

(87) PCT Pub. No.: WO02/064700
PCT Pub. Date: Aug. 22, 2002

(65) Prior Publication Data
US 2004/0142208 A1 Jul. 22, 2004

(30) Foreign Application Priority Data

Feb. 14, 2001 (JP) .................................. 2001-036634
Feb. 7, 2002 (JP) .................................. 2002-030753

(51) Int. Cl.
*H01L 51/54* (2006.01)
*C09K 11/06* (2006.01)

(52) U.S. Cl. . 428/690; 428/917; 313/504; 257/E51.044; 546/4; 546/10

(58) Field of Classification Search ........................ None
See application file for complete search history.

(56) References Cited

U.S. PATENT DOCUMENTS

| | | | |
|---|---|---|---|
| 6,312,839 B1 | 11/2001 | Kim et al. | |
| 2001/0019782 A1 | 9/2001 | Igarashi et al. | |
| 2002/0034656 A1* | 3/2002 | Thompson et al. | 428/690 |
| 2002/0055014 A1 | 5/2002 | Okada et al. | |
| 2002/0063516 A1 | 5/2002 | Tsuboyama et al. | |
| 2003/0054198 A1 | 3/2003 | Tsuboyama et al. | |
| 2005/0003233 A1 | 1/2005 | Igarashi et al. | |
| 2005/0025996 A1 | 2/2005 | Tsuboyama et al. | |
| 2005/0266268 A1 | 12/2005 | Tsuboyama et al. | |

FOREIGN PATENT DOCUMENTS

| | | |
|---|---|---|
| EP | 1 191 612 A2 | 3/2002 |
| EP | 1 238 981 A2 | 9/2002 |
| JP | 2001-247859 A | 9/2001 |
| JP | 2001-345183 A | 12/2001 |
| JP | 2002-319491 A | 10/2002 |
| JP | 2003-81988 A | 3/2003 |
| JP | 2003-81989 A | 3/2003 |
| JP | 2003-515897 A | 5/2003 |
| KR | 10-2000-0075253 | 12/2000 |
| WO | WO 01/41512 A1 | 6/2001 |
| WO | WO 02/02714 A2 | 1/2002 |

OTHER PUBLICATIONS

Chihaya Adachi, et al., Appl. Phys. Lett., vol. 55 (15), pp. 1489-1491 (1989).
C.W. Tang, et al., Appl. Phys. Lett., vol. 51 (12), pp. 913-915 (1987).
S.A. Van Slyke, et al., Appl. Phys. Lett., vol. 69 (15), pp. 2160-2162 (1996).
M.A. Baldo, et al., "Very High-Efficiency Green Organic Light-Emitting Devices Based on Electrophosphorescence". Applied Physics Letters, Jul. 1999, vol. 75, No. 1, pp. 4-6.
U.S. Appl. No. 60/215,362, filed Jun. 30, 2000.
U.S. Appl. No. 60/224,273, filed Aug. 10, 2000.
Japanese Office Action Issued in corresponding Japanese Patent Application No. 2002-565020, dated Nov. 28, 2006.
Korean Office Action, with Partial English Translation, issued in Korean Patent Application No. KR 10-2002-701316 dated on Sep. 25, 2008.

* cited by examiner

*Primary Examiner* — Marie R. Yamnitzky
(74) *Attorney, Agent, or Firm* — McDermott Will & Emery LLP

(57) ABSTRACT

In an organic EL device, a hole injection electrode is formed on a glass substrate, and a hole injection layer, a hole transport layer and a luminescent layer are formed in turn on the hole injection electrode. An electron injection electrode is formed on the luminescent layer. The luminescent layer includes an organic iridium compound composed of a combination of a quinoline derivative and iridium. This organic iridium compound can emit red-orange light via a triplet excited state.

2 Claims, 2 Drawing Sheets

ORGANIC ELECTROLUMINESCENT DEVICE, LUMINESCENT MATERIAL AND ORGANIC COMPOUND

TECHNICAL FIELD

The present invention relates to an organic electroluminescent device, a luminescent material and an organic compound.

BACKGROUND ART

Organic electroluminescent devices (hereinafter referred to as organic EL devices) are expected as new self-light emitting devices. An organic EL device has a stacked layered structure that a carrier transport layer (an electron transport layer or a hole transport layer) and a luminescent layer are formed between a hole injection electrode and an electron injection electrode.

Electrode materials having a large work function such as gold or ITO (indium-tin oxide) are employed for the hole injection electrode, while those having a small work function such as Mg (magnesium) or Li (lithium) are employed for the electron injection electrode.

Organic materials are employed for the hole transport layer, the luminescent layer and the electron transport layer. Materials having the property of a p-type semiconductor are employed for the hole transport layer, while those having the property of an n-type semiconductor are employed for the electron transport layer. The luminescent layer is also composed of organic materials that have carrier transportability such as electron transportability or hole transportability and emit fluorescence or phosphorescence.

These hole injection electrode, hole transport layer, luminescent layer, electron transport layer and electron injection electrode are stacked in turn to form the organic EL device.

Each function layer such as the hole transport layer, the electron transport layer and the luminescent layer is constituted by a plurality of layers or omitted depending on the organic materials to be used.

In such an elementary structure as shown in Appl. Phys. Lett., Vol. 55, pp. 1489-1491 by Chihaya Adachi et al., for example, only two organic layers, which are a luminescent layer and an electron transport layer exist between a hole injection electrode and an electron injection electrode. This is because the luminescent layer composed of luminescent materials called NSD has excellent hole transportability and hence serves also as a hole transport layer.

Further, the elementary structure shown in Appl. Phys. Lett., Vol. 51, pp. 913-915 (1987) by C. W. Tang et al. is constituted by two organic layers, which are a hole transport layer and a luminescent layer. In this case, tris(8-hydroxyquinolinato)aluminum (hereinafter referred to as Alq) contained in the luminescent layer serves to both emit light and transport electrons.

On the other hand, the elementary structure shown in Appl. Phys. Lett., Vol. 69, pp. 2160-2162(1996) by S. A. Van Slyke et al. is constituted by three organic layers, which are a hole injection layer, a hole transport layer and a luminescent layer. In this case, the hole injection layer is composed of copper phthalocyanine, serving for the same function as the hole transport layer, which results in two hole transport layers existing in the entire device.

Thus, the number of the electron transport layer, hole transport layer and luminescent layer can freely be adjusted depending on the organic materials to be used.

In the organic EL devices, visible light of blue through red can be obtained by selecting the organic materials constituting the luminescent layers. Accordingly, a full-color display can be realized by use of organic EL devices that emit respective monochromatic lights of red, green and blue which are three primary colors (RGB) of light.

In red light, green light and blue light obtained from the organic EL devices, the green and blue lights are stable light. In contrast, as for red through orange light, i.e., red-orange light, it is difficult to obtain the light with high luminance and high luminous efficiency. This is because there exist no solid organic materials that emit fluorescence or phosphorescence of red to orange at high efficiency.

For example, as the organic materials for the luminescent layers of the organic EL devices that emit red-orange light, DCM-based materials being laser dye-based materials such as 4-(dicyanomethylene)-2-methyl-6-julodin-4-yl-vinyl)-4H-pyran (hereinafter referred to as DCM) and the like that has such a structure as represented mainly by a formula (10) shown below are employed. In such organic EL devices employing the DCM-based materials, however, luminous efficiency can hardly be increased.

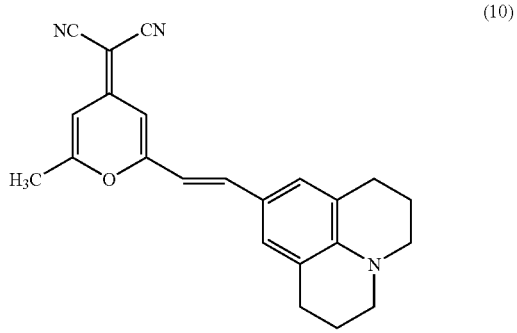

(10)

DISCLOSURE OF THE INVENTION

An object of the present invention is to provide an organic EL device in which red-orange light with high luminance can be obtained at high luminous efficiency.

Another object of the present invention is to provide a luminescent material in which red-orange light with high luminance can be obtained at high luminous efficiency.

Still another object of the present invention is to provide an organic compound for use in an organic EL device in which red-orange light with high luminance can be obtained at high luminous efficiency.

An organic electroluminescent device according to one aspect of the present invention includes a hole injection electrode, an electron injection electrode, and a luminescent layer provided between the hole injection electrode and the electron injection electrode, and the luminescent layer includes a compound composed of iridium and a quinoline derivative.

In the organic electroluminescent device according to the present invention, the luminescent layer includes the compound composed of iridium and the quinoline derivative.

Since the compound composed of iridium and the quinoline derivative is a material capable of emitting light via a triplet excited state, the luminescent layer of the above organic electroluminescent device can emit red-orange light by effectively utilizing the triplet excited state which cannot usually be used effectively.

Thus, it becomes possible to realize red-orange light emission with high luminance at high luminous efficiency in the above organic electroluminescent device.

In the above organic electroluminescent device, the luminescent layer per se may be composed of the compound comprised of iridium and the quinoline derivative. Alternatively, the compound composed of iridium and the quinoline derivative may be added as a dopant to the luminescent layer.

It is preferable that the compound composed of iridium and the quinoline derivative has a molecular structure represented by a formula (1) below:

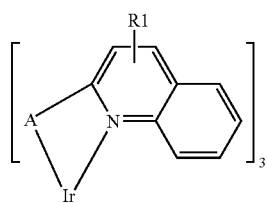

(1)

where R1 is a hydrogen atom, a halogen atom or a substituent, and that A is a substituent.

The luminescent layer comprised of the compound having such a molecular structure can emit red-orange light via the triplet excited state. This makes it possible to realize red-orange light emission with high luminance at high luminous efficiency.

In the compound represented by the formula (1), A may have a molecular structure represented by a formula (A1) below:

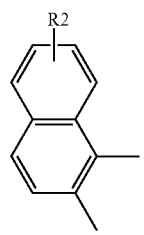

(A1)

where R2 may be a hydrogen atom, a halogen atom or a substituent.

In the compound represented by the formula (1), A may have a molecular structure represented by a formula (A2) below:

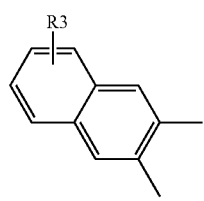

(A2)

where R3 may be a hydrogen atom, a halogen atom or a substituent.

In the compound represented by the formula (1), A may have a molecular structure represented by a formula (A3) below:

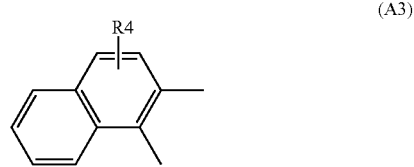

(A3)

where R4 may be a hydrogen atom, a halogen atom or a substituent.

In the compound represented by the formula (1), A may have a molecular structure represented by a formula (A4) below:

(A4)

where R5 may be a hydrogen atom, a halogen atom or a substituent.

In the compound represented by the formula (1), A may have a molecular structure represented by a formula (A5) below:

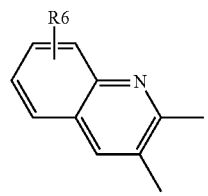

(A5)

where R6 may be a hydrogen atom, a halogen atom or a substituent.

In the compound represented by the formula (1), A may have a molecular structure represented by a formula (A6) below:

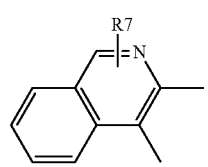

(A6)

where R7 may be a hydrogen atom, a halogen atom or a substituent.

In the compound represented by the formula (1), A may have a molecular structure represented by a formula (A7) below:

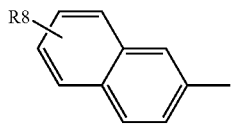
(A7)

where R8 may be a hydrogen atom, a halogen atom or a substituent.

In the compound represented by the formula (1), A may have a molecular structure represented by a formula (A8) below:

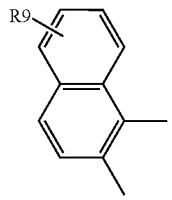
(A8)

where R9 may be a hydrogen atom, a halogen atom or a substituent.

In the compound represented by the formula (1), A may have a molecular structure represented by a formula (A9) below:

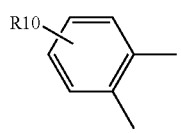
(A9)

where R10 may be a hydrogen atom, a halogen atom or a substituent.

In the compound represented by the formula (1), A may have a molecular structure represented by a formula (A10) below:

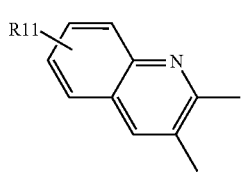
(A10)

where R11 may be a hydrogen atom, a halogen atom or a substituent.

In the compound represented by the formula (1), A may have a molecular structure represented by a formula (A11) below:

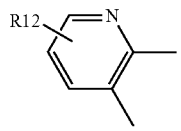
(A11)

where R12 may be a hydrogen atom, a halogen atom or a substituent.

It is preferable that the compound composed of iridium and the quinoline derivative has a molecular structure represented by a formula (2) below:

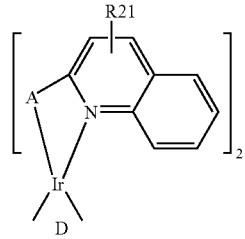
(2)

where R21 is a hydrogen atom, a halogen atom or a substituent, A is a substituent, and D is a substituent forming a ring.

D may have a molecular structure represented by a formula (D1) below:

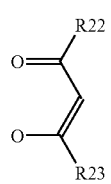
(D1)

where R22 and R23, which may be identical to or different from each other, may be a hydrogen atom, a halogen atom or a substituent.

D may have a molecular structure represented by a formula (D2) below:

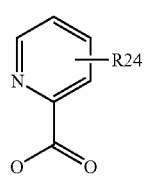
(D2)

where R24 may be a hydrogen atom, a halogen atom or a substituent.

In the compound represented by the formula (2), A may have a molecular structure represented by a formula (A12) below:

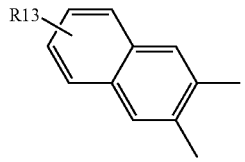

(A12)

where R13 may be a hydrogen atom, a halogen atom or a substituent.

In the compound represented by the formula (2), A may have a molecular structure represented by a formula (A13) below:

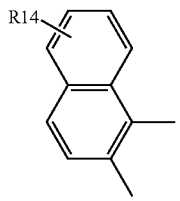

(A13)

where R14 may be a hydrogen atom, a halogen atom or a substituent.

In the compound represented by the formula (1), A may have a molecular structure represented by a formula (A14) below:

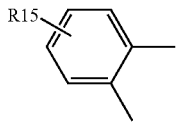

(A14)

where R15 may be a hydrogen atom, a halogen atom or a substituent.

In the compound represented by the formula (1), A may have a molecular structure represented by a formula (A15) below:

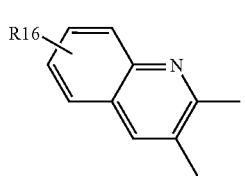

(A15)

where R16 may be a hydrogen atom, a halogen atom or a substituent.

In the compound represented by the formula (1), A may have a molecular structure represented by a formula (A16) below:

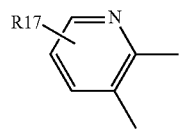

(A16)

where R17 may be a hydrogen atom, a halogen atom or a substituent.

The compound composed of iridium and a quinoline derivative may be tris(2-phenylquinoline)iridium having a molecular structure represented by a formula (8) below.

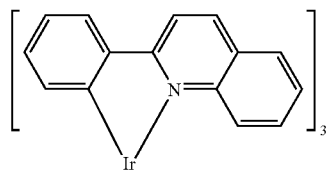

(8)

The luminescent layer may further include a host material, and the content of the compound composed of iridium and the quinoline derivative may be not less than 0.1 wt % nor more than 50 wt % for the host material. As described above, even if the compound composed of iridium and a quinoline derivative is added as a dopant to the luminescent layer, red-orange light with high luminance can be obtained at high luminous efficiency.

The host material may be 4,4'-bis(carbazol-9-yl)biphenyl having the molecular structure represented by a formula (9) shown below.

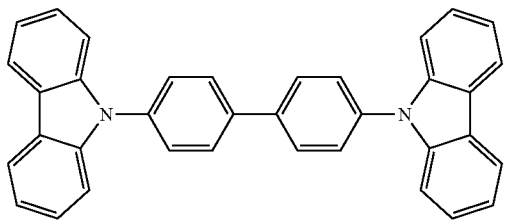

(9)

The use of such a host material allows the achievement of red-orange light with high luminance at high luminous efficiency.

A hole blocking layer with a larger ionization potential than that of the luminescent layer is preferably provided between the luminescent layer and the electron injection electrode. The provision of such a hole blocking layer results in an increase in the energy barrier between the luminescent layer and the hole blocking layer. This makes it possible to prevent the injection of holes from the luminescent layer to the electron injection electrode and thus re-couple electrons and holes at high efficiency in the luminescent layer. This enables improvements in the luminous efficiency of the organic EL devices.

A luminescent material according to another aspect of the present invention has a molecular structure represented by a formula (2) below:

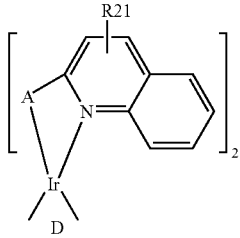
(2)

where R21 is a hydrogen atom, a halogen atom or a substituent, A is a substituent, and D is a substituent forming a ring.

D may have a molecular structure represented by a formula (D1) below:

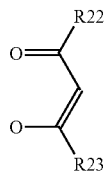
(D1)

where R22 and R23, which may be identical to or different from each other, may be a hydrogen atom, a halogen atom or a substituent.

D may have a molecular structure represented by a formula (D2) below:

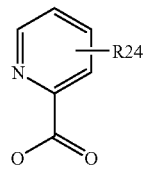
(D2)

where R24 may be a hydrogen atom, a halogen atom or a substituent.

Such a luminescent material can emit red-orange light since it is such a material that can emit light via a triplet excited state.

An organic compound according to still another aspect of the present invention has a molecular structure represented by a formula (2) shown below:

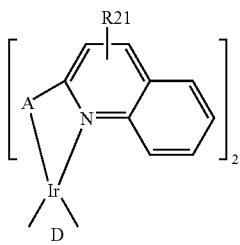
(2)

where R21 is a hydrogen atom, a halogen atom or a substituent, A is a substituent, and D is a substituent forming a ring.

D may have a molecular structure represented by a formula (D1) shown below:

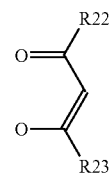
(D1)

where R22 and R23, which may be identical to or different from each other, may be a hydrogen atom, a halogen atom or a substituent.

D may have a molecular structure represented by a formula (D2) shown below:

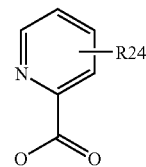
(D2)

where R24 may be a hydrogen atom, a halogen atom or a substituent.

The organic compound may have a molecular structure represented by a formula (C1) shown below.

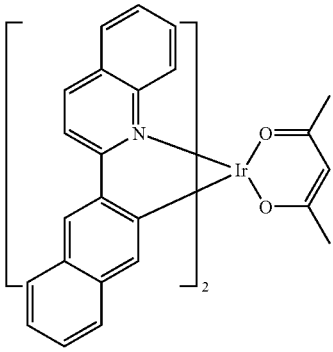
(C1)

The organic compound may have a molecular structure represented by a formula (C2) shown below.

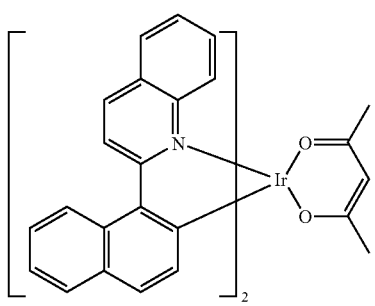
(C2)

The organic compound may have a molecular structure represented by a formula (C7) shown below.

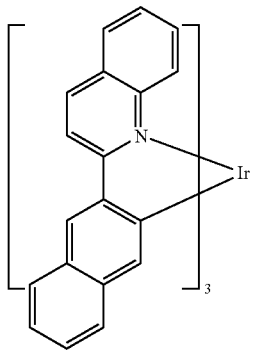

(C7)

The organic compound may have a molecular structure represented by a formula (C8) shown below.

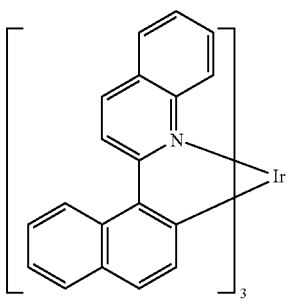

(C8)

Such an organic compound can emit red-orange light since it is such a material that can emit light via a triplet excited state.

BEST MODE FOR CARRYING OUT THE INVENTION

Figure 1:
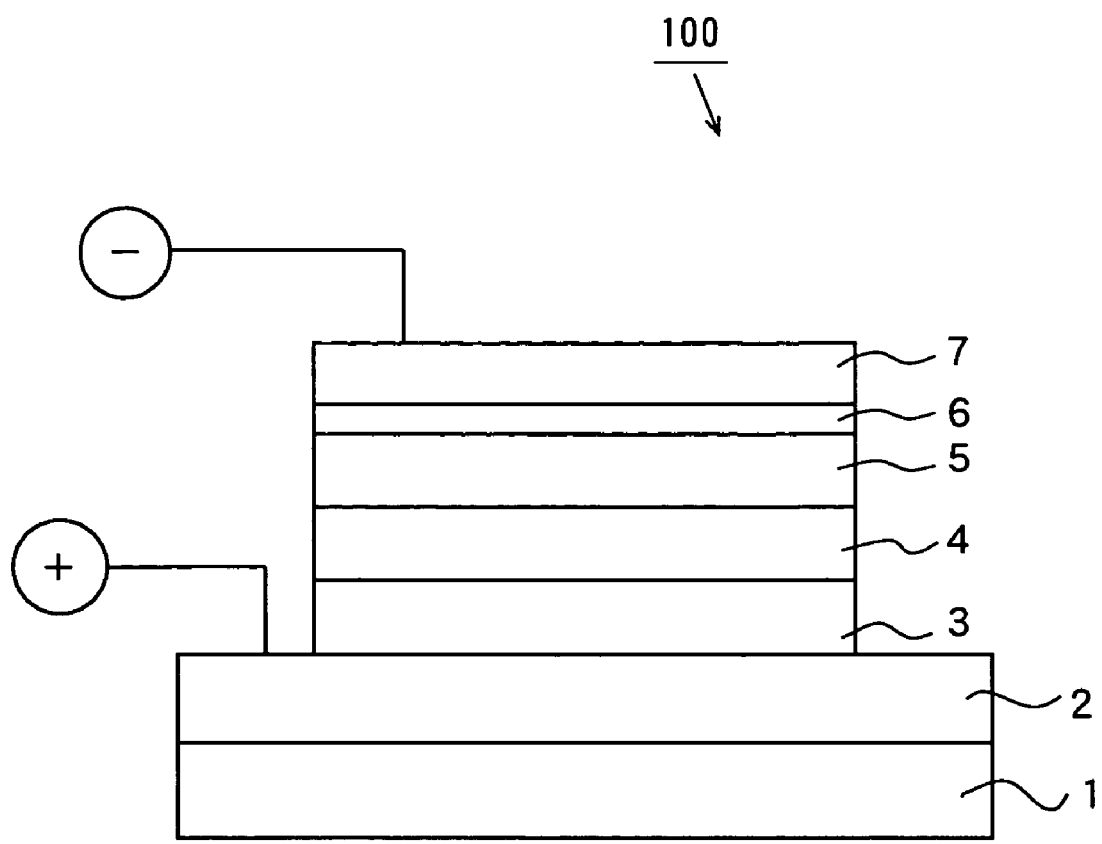
FIG. 1 is a schematic diagram showing the structure of an organic EL device according to one embodiment of the present invention.

FIG. 1 is a schematic diagram showing the structure of an organic electroluminescence (hereinafter referred to as an organic EL device) according to one embodiment of the present invention.

With reference to FIG. 1, a hole injection electrode (an anode) 2 composed of a transparent electrode film is formed on a glass substrate 1, in an organic EL device 100. A hole injection layer 3, a hole transport layer 4 and a luminescent layer 5 all made of respective organic materials are formed in turn on the hole injection electrode 2. A hole blocking layer 6 made of organic materials is formed on the luminescent layer 5, and an electron injection electrode (a cathode) 7 is formed on the hole blocking layer 6.

The luminescent layer 5 includes an organic iridium compound composed of a quinoline derivative and iridium being metal. The luminescent layer 5 per se may be composed of such an organic iridium compound. Alternatively, the layer 5 may include such an organic iridium compound as a luminescent dopant.

In this embodiment, for example, the organic iridium compound composed of iridium and the quinoline derivative is contained as the luminescent dopant in a host material which will be described later. The content of this organic iridium compound is 0.1 wt % to 50 wt %, preferably 1 wt % to 10 wt % for the host material.

As the host material, 4,4'-bis(carbazol-9-yl)biphenyl (hereinafter referred to as CBP) having the molecular structure represented by, e.g., a formula (9) shown below is employed.

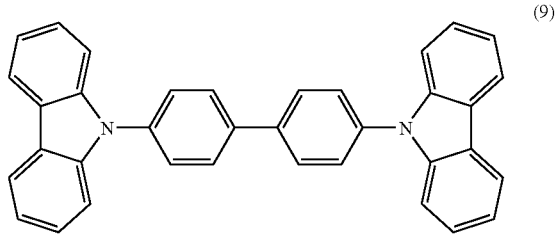

(9)

It is preferable that the above described organic iridium compound contained in the luminescent layer 5 has such a molecular structure as represented by a formula (1) shown below:

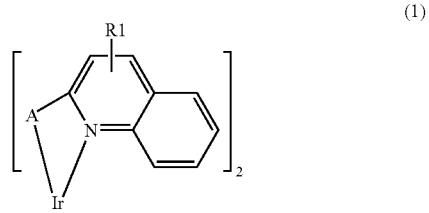

(1)

where R1 represents a hydrogen atom, a halogen atom or a substituent, and A represents a substituent which will be described later.

For example, R1 is $-C_nH_{2n+1}$ (n=0 to 10), a phenyl group, a naphthyl group, $-CN$, $-N(C_nH_{2n+1})_2$ (n=1 to 10), $-COOC_nH_{2n+1}$ (n=1 to 10), $-F$, $-Cl$, $-Br$, $-I$, $-OCH_3$, $-OC_2H_5$ and so on.

In the above formula (1), A may be any one of substituents each having such molecular structures as represented by, for example, respective formulas (A1) to (A11).

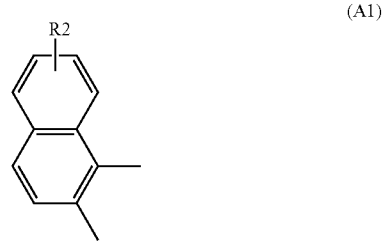

(A1)

(A2) 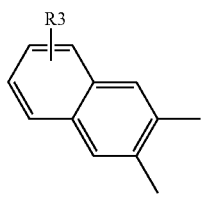

(A3) 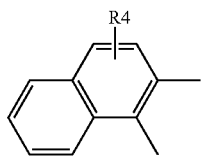

(A4) 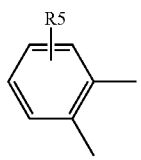

(A5) 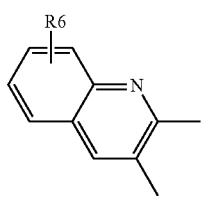

(A6) 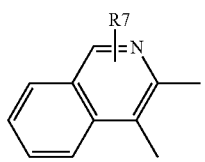

(A7) 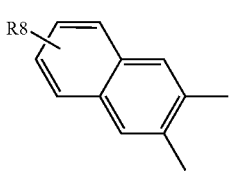

(A8) 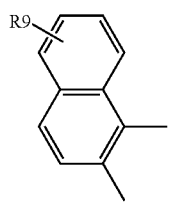

(A9) 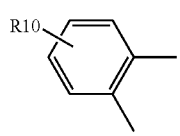

(A10) 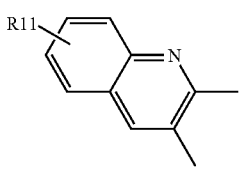

(A11) 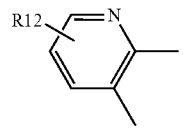

In the formulas (A1) to (A11), R2 to R12 are a hydrogen atom, a halogen atom or a substituent. For example, R8 to R12 are $-C_nH_{2n+1}$ (n=10 to 10), a phenyl group, a naphthyl group, $-CN$, $-N(C_nH_{2n+1})_2$ (n=1 to 10), $-COOC_nH_{2n+1}$ (n=1 to 10), $-F$, $-Cl$, $-Br$, $-I$, $-OCH_3$, $-OC_2H_5$ and so on.

Thus, the organic iridium compound composed of iridium and the quinoline derivative, represented by the above formula (1) is capable of emitting phosphorescence of red to orange via a triplet excited state.

The organic iridium compound represented by the above formula (1) is produced by making the reaction between a quinoline derivative having a molecular structure represented by a formula (B1) shown below and an iridium compound, in which reaction the quinoline derivative is coordinated or chelated with iridium. In this case, not less than 3 mol of the quinoline derivative is reacted with 1 mol of the iridium compound. As the iridium compound, tris(acetylacetonato) iridium (Ir(acac)$_3$), or iridium chloride or the like can be employed. Here, "acac" is an abbreviation of "acetylacetone."

(B1) 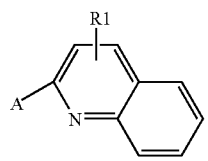

According to quantum mechanical studies, it is considered that out of the entire excited state caused by coupling of electrons and holes, the triplet excited state where electron spin is parallel is generated at a ratio of approximately ¾, while the singlet excited state where electron spin is reverse parallel and the sum of spin quantum numbers is 0 is generated at a ratio of approximately ¼.

The light emission which is caused when electrons being in the singlet excited state out of such two types of excited states transit to a ground state is called fluorescence. Such fluorescence is generated based on a spin allowable state and easily occurs. Thus, the fluorescence is applied in wide use for luminescent phenomena such as of organic EL devices and the like.

On the other hand, the light emission which is caused when electrons being in the triplet excited state transit to the ground state is called phosphorescence. The phosphorescence is generated based on a spin inhibited state. According to Pauli's exclusion principle, it is not possible that two electrons with parallel electron spin exist on the same electron orbit (which corresponds to the ground state in this case). Therefore, the electron spin of electrons which may transit is required to be inverted by receiving some perturbation, in order that the electrons being in the triplet excited state may transit to the ground state and emit light. However, the inversion of electron spin is difficult in most of luminescent substances which are usually used for the organic EL devices. Therefore, as for normal substances, phosphorescence is known as a special phenomenon which is observed only in a very low temperature area equal to or below a liquid nitrogen temperature.

For example, the above described DCM-based material employed as luminescent materials for a conventional red light emitting organic EL device emits red fluorescence via the singlet excited state, and thus this material cannot effectively utilize the triplet excited state covering approximately ¾ of the entire excited state. It is therefore difficult to achieve the increased luminous efficiency in the organic EL devices having the luminescent layer made of such DCM-based red luminescent materials.

In contrast, as to the organic EL device 100 of this embodiment, as described above, since the luminescent layer 5 includes, as the red-orange light emitting materials, the organic iridium compound having the structure represented by the above formula (1), the luminescent layer 5 can emit red-orange phosphorescence via the triplet excited state. Thus, it is possible to effectively use the triplet excited state covering approximately ¾ of the entire excited state, in this case. This makes it possible to obtain red-orange light with high luminance and at high luminous efficiency in the organic EL device 100.

M. A. Bald et al. disclose in Applied Physics Letters, Vol. 75, No. 1, p. 4 (1999) an organic iridium compound having a structure similar to that of the organic iridium compound having the molecular structure represented by the above formula (1). The disclosed organic iridium compound is, however, a compound comprised of a combination of phenylpyridine and iridium, and hence its π conjugated electron system is shorter than that of the compound comprised of the combination of the quinoline derivative and iridium as in this embodiment. Therefore, the color of light emitted from the organic iridium compound composed of phenylpyridine and iridium disclosed in the above document is green.

On the other hand, in this embodiment, since the organic iridium compound composed of the combination of the quinoline derivative and iridium is employed, its π conjugated electron system can be extended compared to that of the above compound composed of phenylpyridine and iridium. This makes it possible to shift a spectrum to a red-orange area, thereby realizing the organic EL device capable of emitting red-orange light in this embodiment.

The above organic iridium compound contained in the luminescent layer 5 preferably has the molecular structure represented by a formula (2) shown below.

R21 represents a hydrogen atom, a halogen atom or a substituent, A represents a substituent which will be described later, and D represents a substituent forming a ring which will be described later.

For example, R21 is —$C_nH_{2n+1}$ (n=10 to 10), a phenyl group, a naphthyl group, —CN, —$N(C_nH_{2n+1})_2$ (n=1 to 10), —$COOC_nH_{2n+1}$ (n=1 to 10), —F, —Cl, —Br, —I, —$OCH_3$, —$OC_2H_5$ and so on.

In the formula (2), D may be a substituent having a molecular structure represented by, for example, a formula (D1) or (D2) shown below.

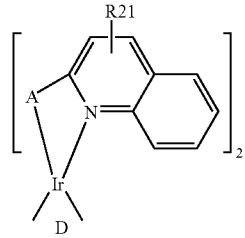

(2)

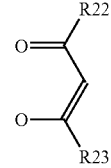

(D1)

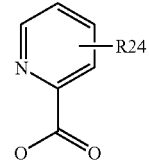

(D2)

In the formula (D1), (D2), R22 to R24 are a hydrogen atom, a halogen atom or a substituent. For example, R22 to R24 are —$C_nH_{2n+1}$ (n=0 to 10), a phenyl group, a naphthyl group, a furyl group, a dienyl group, —$N(C_nH_{2n+1})_2$ (n=1 to 10), —$COOC_nH_{2n+1}$ (n=1 to 10), —F, —Cl, —Br, —I, —$CF_3$ and the like.

In the formula (2), A may be any one of substituents having the molecular structures represented by, for example, formulas (A12) to (A16) shown below.

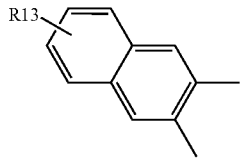

(A12)

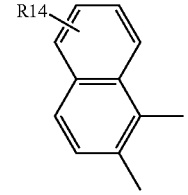

(A13)

(A14)

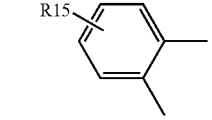

(A15)

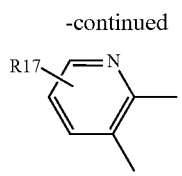

(A16)

In the formulas (A12) to (A16), R13 to R17 are a hydrogen atom, a halogen atom or a substituent. For example, R13 to R17 are —$C_nH_{2n+1}$ (n=1 to 10), a phenyl group, a naphthyl group, —CN, —$N(C_nH_{2n+1})_2$ (n=1 to 10), —$COOC_nH_{2n+1}$ (n=1 to 10), —F, —Cl, —Br, —I, —$OCH_3$, —$OC_2H_5$ and so on.

Thus, the organic iridium compound composed of iridium and the quinoline derivative, represented by the above formula (2) is capable of emitting phosphorescence of red to orange via a triplet excited state.

The organic iridium compound represented by the above formula (2) is produced by the reaction among a quinoline derivative having a molecular structure represented by a formula (B2) shown below, an iridium compound and a compound corresponding to D represented by the above formula (D1) or (D2), in which reaction the quinoline derivative and D are coordinated or chelated with iridium. In this case, 1.5 to 2.5 mol of the quinoline derivative and 0.5 to 1.5 mol of the compound corresponding to D are reacted with 1 mol of the iridium compound. As the iridium compound, tris(acetylacetonato)iridium ($Ir(acac)_3$), or iridium chloride or the like can be employed. Here, "acac" is an abbreviation of "acetylacetone."

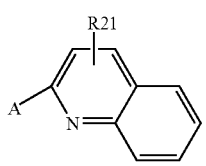

(B2)

The structure of the organic EL device according to the present invention is not limited to the above structure, but can apply various structures. For example, such a structure may be applied that only two layers, which are the luminescent layer and the electron transport layer are provided between the hole injection electrode 2 and the electron injection electrode 7. Alternatively, such a structure may be applied that the hole transport layer, the luminescent layer, the hole blocking layer and the electron transport layer are stacked in turn between the hole injection electrode 2 and the electron injection electrode 7.

A hole blocking layer having a larger ionization potential than that of the luminescent layer is preferably provided between the luminescent layer and the electron injection electrode in the organic EL device. Provision of this hole blocking layer enables the increased energy barrier between the luminescent layer and the hole blocking layer. This can prevent the injection of holes from the luminescent layer to the layers on the side of the electron injection electrode (e.g., the electron transport layer and the electron injection layer), enabling the re-coupling of holes and electrons in the luminescent layer at high efficiency. This results in improvements in the luminous efficiency in the organic EL device.

In the above organic EL device 100, when a voltage is applied across the hole injection electrode 2 and the electron injection electrode 7, the luminescent layer 5 emits red-orange light, and light is emitted from the back face of the glass substrate 1.

EXAMPLES

Respective organic EL devices of inventive examples 1 to 3 and a comparative example were manufactured, and their luminescent characteristics were measured as in the following.

Inventive Example 1

In the inventive example 1, such an organic EL device was used that a hole injection electrode (an anode), a hole transport layer, a luminescent layer, a hole blocking layer, an electron transport layer and an electron injection electrode (a cathode) were stacked in turn on a glass substrate.

In this case, the hole injection electrode of the organic EL device is composed of indium-tin oxides (ITO) with a 1000 Å thickness. The hole transport layer has a 500 Å thickness and is composed of N,N'-Di(naphthalen-1-yl)-N,N'-diphenylbenzidine (hereinafter referred to as NPB) having the molecular structure represented by a formula (11) as shown below.

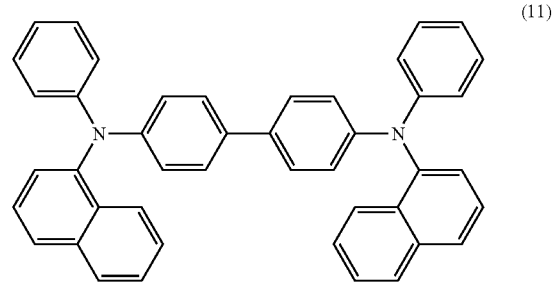

(11)

The luminescent layer 5 has a 200 Å thickness, and it contains, as a host material, CBP having the molecular structure represented by a formula (9) shown below and contains, as a red-orange luminescent dopant, tris(2-phenylquinoline) iridium (hereinafter referred to as $Ir(Phq)_3$) having the molecular structure represented by a formula (8) shown below. This $Ir(Phq)_3$ can emit red-orange light via the triplet excited state.

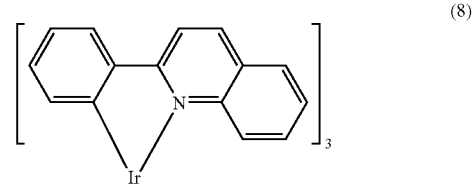

(8)

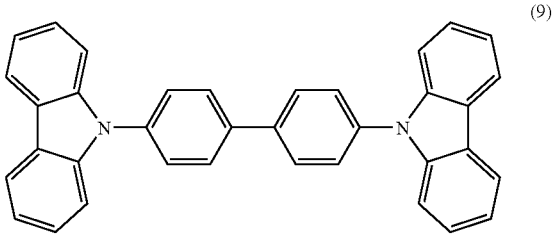

(9)

In this instance, the luminescent layer 5 contains 6.5 wt % of Ir(Phq)$_3$ for the CBP serving as the host material. Further, the ionization potential of CBP is 5.9 eV.

The hole blocking layer has a 100 Å thickness and is composed of Bathocuproine (hereinafter referred to as BCP) having the molecular structure represented by a formula (12). The ionization potential of the hole blocking layer composed of BCP is 6.2 eV, which is larger than that of CBP serving as the host material of the luminescent layer.

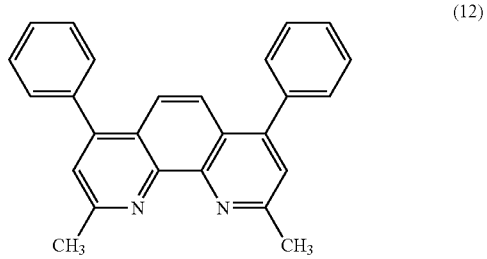

(12)

The electron transport layer has a 150 Å thickness and is composed of tris(8-hydroxyquinolinato)aluminum (hereinafter referred to as Alq) having the molecular structure represented by a formula (13). The ionization potential of the electron transport layer composed of Alq is 5.5 eV.

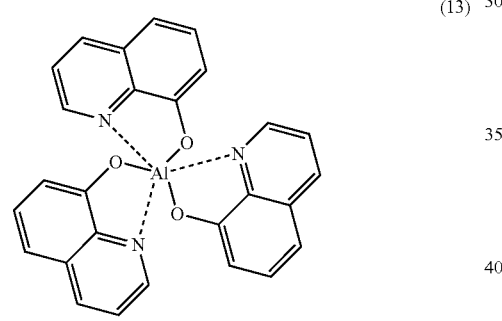

(13)

The energy barrier generated between the luminescent layer and the hole blocking layer becomes increased in the organic EL device of the inventive example 1, in which the hole blocking layer with a large ionization potential as described above is formed between the luminescent layer and the electron transport layer. This can prevent the injection of holes from the luminescent layer to the electron transport layer. This enables the re-coupling of holes and electrons in the luminescent layer at high efficiency. This results in improvements of luminous efficiency in the organic EL device.

Further, the electron injection electrode is composed of a MgIn alloy (a ratio of 10 to 1) with a 2000 Å thickness.

The organic EL device having the above described structure was manufactured as in the following manner.

First, the hole injection electrode made of indium-tin oxides (ITO) was formed on the glass substrate. Then, the glass substrate with the hole injection electrode formed thereon was cleaned with a neutral detergent, followed by ultrasonic cleaning in acetone for 10 minutes and in ethanol for 10 minutes. Further, the surface of the glass substrate was cleaned in an ozone cleaner.

After that, the hole transport layer, the luminescent layer, the hole blocking layer, the electron transport layer and the electron injection electrode were stacked in turn by a vacuum vapor deposition on the above hole injection electrode made of ITO. This vapor deposition was conducted under conditions of ordinary temperatures without control of substrate temperatures at the degree of vacuum of $1 \times 10^{-6}$ Torr.

A positive bias voltage was applied to the hole injection electrode of the organic EL device manufactured by the above method, while a negative bias voltage was applied to the electron injection electrode, so that the luminescent characteristics of the device were measured.

As the result of the measurement of the luminescent characteristics of the organic EL device as above, excellent orange light with a peak at a 586 nm wavelength was obtained. This obtained orange light exhibited the relation x=0.53 and y=0.46 at a CIE (Commission International d'Eclairage) chromaticity coordinate where x indicates the abscissa, y indicates the ordinate of the coordinate.

In this case, the maximal luminance of the organic EL device was 34,200 cd/m$^2$, and the luminous efficiency at that time was 15.7 cd/A.

Inventive Example 2

In the inventive example 2, an organic EL device was employed that has the same structure as that of the organic EL device of the inventive example 1 except for the following points. The organic EL device of the inventive example 2 was manufactured by the same method as that of the organic EL device of the inventive example 1.

In the organic EL device of the inventive example 2, the hole blocking layer is composed of (1,1'-Bisphenyl)-4-Olato) (2-methyl-8-quinolinolate-N1,08)Aluminum (hereinafter referred to as BAlq) having the molecular structure represented by a formula (14) shown below. This hole blocking layer composed of BAlq has a 100 Å thickness and a 5.6 eV ionization potential.

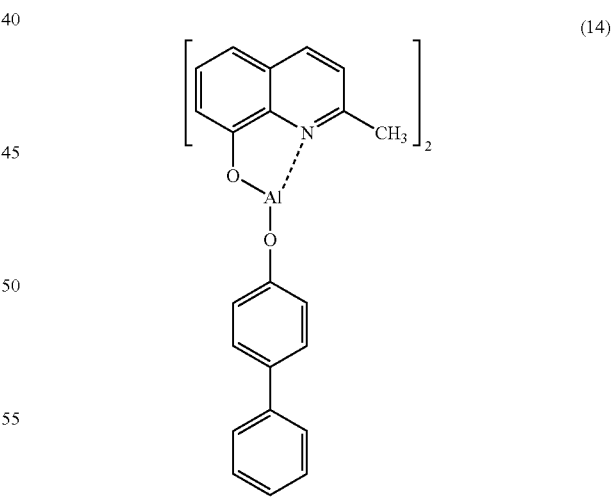

(14)

In the organic EL device of this example, in which the hole blocking layer with the large ionization potential as above is formed between the luminescent layer and the electron transport layer, the energy barrier generated between the luminescent layer and the hole blocking layer is increased, thereby preventing the injection of holes from the luminescent layer to the electron transport layer. This enables the re-coupling of holes and electrons in the luminescent layer at high efficiency.

This results in improvements of luminous efficiency in the organic EL device. The luminescent characteristics of the above organic EL device were measured by the same method as that applied in the inventive example 1. Consequently, excellent orange light with a peak at a 583 nm wavelength was obtained in this organic EL device. This obtained orange light exhibited the relation x=0.53 and y=0.46 at the CIE chromaticity coordinate. In this case, the maximal luminance of the organic EL device was 38,700 cd/m$^2$, and its luminous efficiency at that time was 14.4 cd/A.

Inventive Example 3

In the inventive example 3, an organic EL device was employed that has the same structure as that of the organic EL device of the inventive example 1 except that the luminescent layer does not include any host material and is composed of only a single layer of Ir(Phq)$_3$ with a 200 Å thickness. The organic EL device of the inventive example 3 was manufactured by the same method as that of the organic EL device of the inventive example 1.

In the organic EL device of this example, since the hole blocking layer with a large ionization potential is formed between the luminescent layer and the electron transport layer, the energy barrier generated between the luminescent layer and the hole blocking layer becomes increased. This can prevent the injection of holes from the luminescent layer to the electron transport layer, thereby enabling the re-coupling of holes and electrons in the luminescent layer at high efficiency. This results in improvements of the luminous efficiency of the organic EL device.

The luminescent characteristics of the above organic EL device were measured by the same method as that applied in the inventive example 1. As a result, excellent orange light with a peak at a 598 nm wavelength was obtained in this organic EL device. The obtained orange light exhibited the relation x=0.57 and y=0.43 at the CIE chromaticity coordinate. The maximal luminance of this organic EL device was 15,560 cd/m$^2$, and its luminous efficiency at this time was 0.2 cd/A.

Comparative Example

In the comparative example, an organic EL device was employed that has the same structure as that of the inventive example 1 except that as the red-orange luminescent dopant of the luminescent layer, Ir(Phq)$_3$ was replaced with 5,10,15, 20-Tetraphenyl-21H,23H-porphine (hereinafter referred to as TPP) having the structure represented by a formula (15) shown below. This organic EL device of the comparative example was manufactured by the same method as that applied to the organic EL device of the inventive example 1. The TPP contained as the red-orange luminescent dopant in the luminescent layer is a substance that emits red-orange light via the singlet excited state.

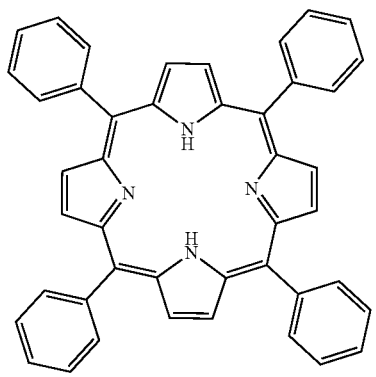

(15)

As for the above organic EL device, its luminescent characteristics were measured by the same method as that applied to the inventive example 1. As a result, red light emission with a peak at a 645 nm wavelength was obtained in this organic EL device. The obtained red light exhibited the relation x=0.65 and y=0.35 at the CIE chromaticity coordinate. The maximal luminance obtained in this case was 100 cd/m$^2$, and the luminous efficiency at this time was 0.1 cd/A.

As has been described above, it was apparent from the inventive examples 1 to 3 and the comparative example that the red-orange light emission with high luminance was realized at excellent luminous efficiency in the organic EL device by use of Ir(Phq)$_3$, which is the triplet excited materials, as the red-orange luminescent dopant of the luminescent layer.

Moreover, as it is apparent from the comparison between the inventive examples 1, 2 and the inventive example 3, the luminance and the luminous efficiency are more increased in the case where the luminescent layer contains BCP or BAlq as a host as compared with the case where the luminescent layer is composed of only Ir(Phq)$_3$.

Inventive Examples 4 to 13

In the inventive examples 4 to 13, such organic EL devices were employed that each has the same structure as that of the organic EL device of the inventive example 1 except for the dopant of the luminescent layer. The organic EL devices of the inventive examples 4 to 13 were manufactured by the same method as that applied to the organic EL device of the inventive example 1.

As the dopants of the luminescent layers included in the respective organic EL devices in the inventive examples 4 to 13, respective compounds 1 to 10 having the molecular structures represented, respectively, by the following formulas (C1) to (C10) were employed.

(C1) 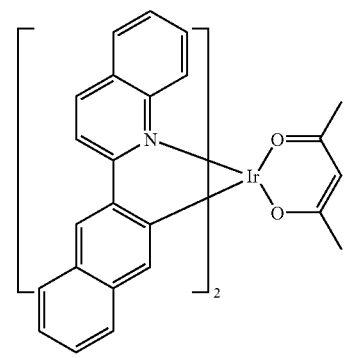
(C2) 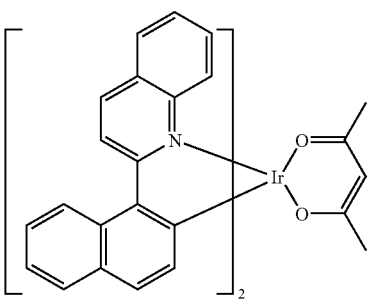
(C3) 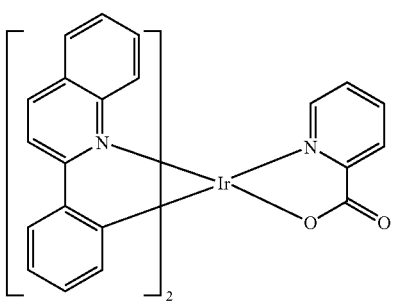
(C4) 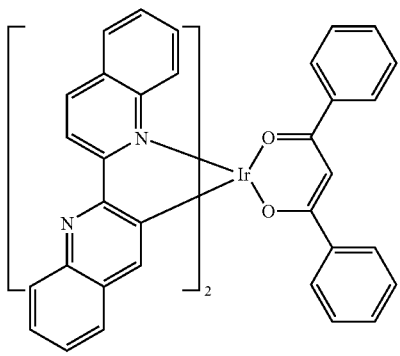
(C5) 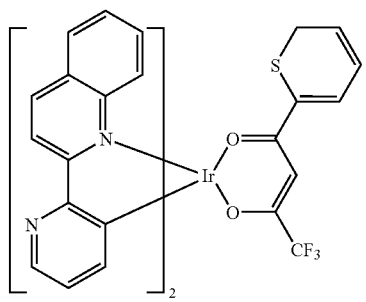
(C6) 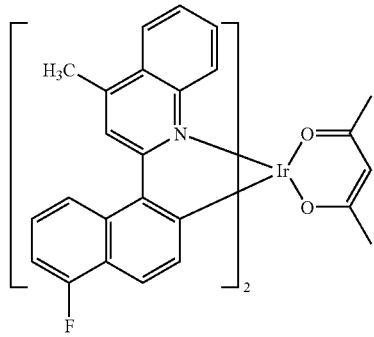
(C7) 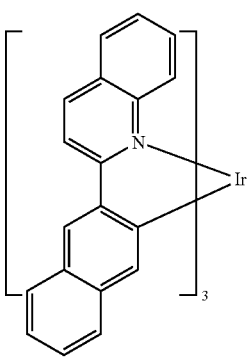
(C8) 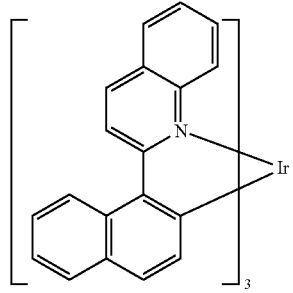
(C9) 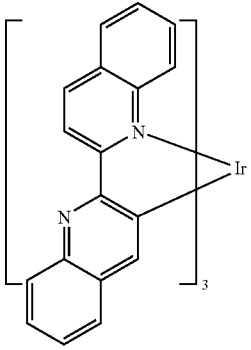

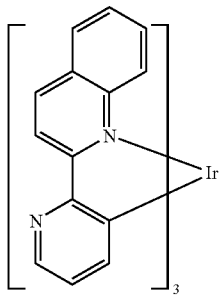
(C10)

Figure 2:
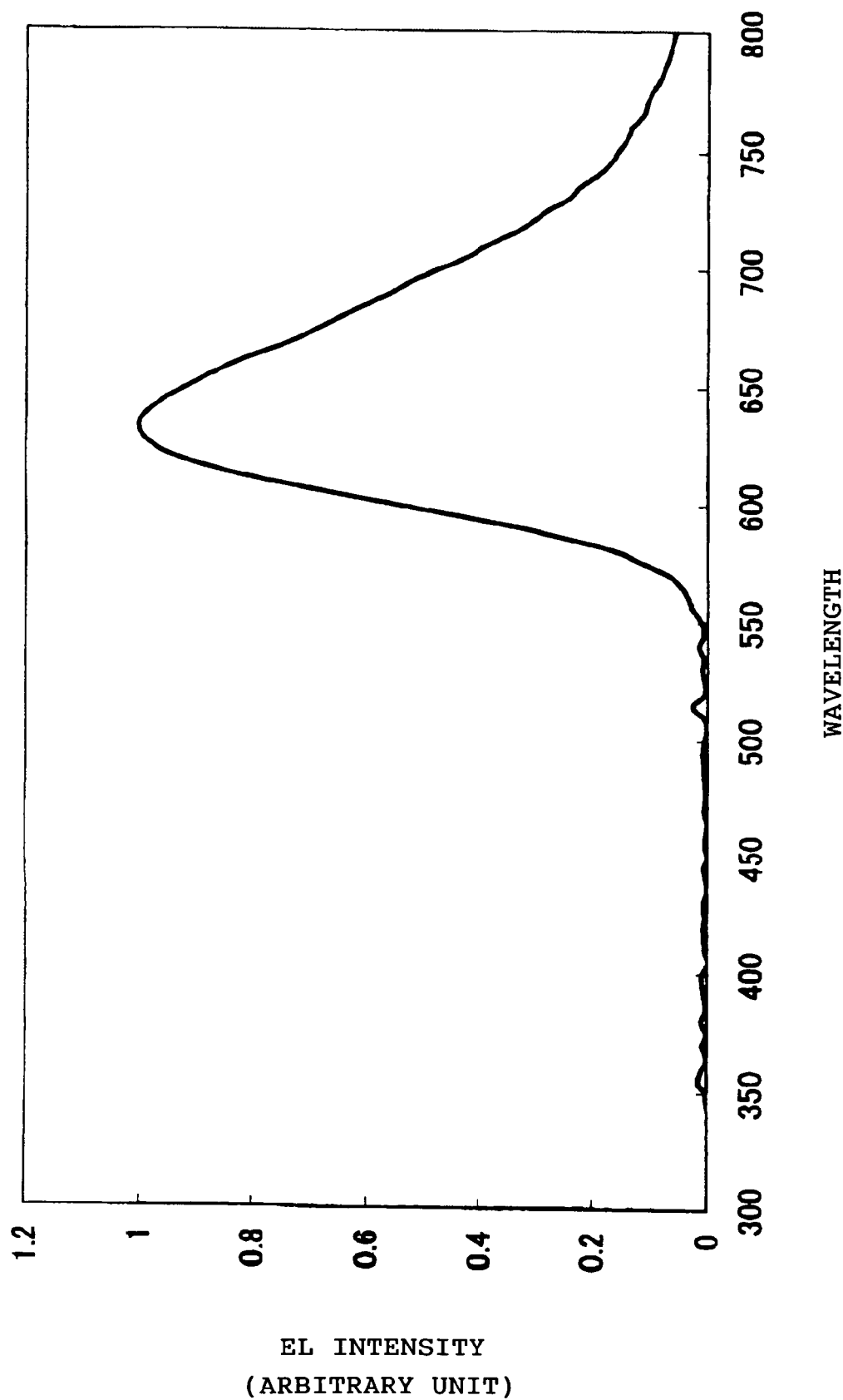
FIG. 2 is a diagram showing a luminescent spectrum in the organic EL device of the embodiment.

The luminescent characteristics of each of the above organic EL devices were measured by the same method as that applied in the inventive example 1. FIG. 2 representatively shows the luminescent spectrum of the organic EL device in the inventive example 11. The luminescent spectrum having a peak at a 630 nm wavelength was obtained in the organic EL device of the inventive example 11, as shown in FIG. 2.

Table 1 shows the results of measurement of the materials and the luminescent characteristics of the organic EL devices in the inventive examples 4 to 13.

TABLE 1

| | Anode | Hole Transport Layer | Luminescent Layer | Hole Blocking Layer | Electron Transport Layer | Cathode | Maximal Luminance (cd/m$^2$) | Luminous Efficiency (cd/A) | Luminous Wavelength (nm) | Chromaticity Coordinate (x, y) |
|---|---|---|---|---|---|---|---|---|---|---|
| Inventive Example 4 | ITO | NPB | CBP(host) + 6.5% compound1 (dopant) | BCP | Alq | MgIn | 12,300 | 5.4 | 625 | 0.64, 0.35 |
| Inventive Example 5 | ITO | NPB | CBP(host) + 6.5% compound2 (dopant) | BCP | Alq | MgIn | 15,800 | 5.6 | 629 | 0.65, 0.34 |
| Inventive Example 6 | ITO | NPB | CBP(host) + 6.5% compound3 (dopant) | BCP | Alq | MgIn | 29,500 | 14.2 | 590 | 0.56, 0.43 |
| Inventive Example 7 | ITO | NPB | CBP(host) + 6.5% compound4 (dopant) | BCP | Alq | MgIn | 11,000 | 4.8 | 623 | 0.64, 0.35 |
| Inventive Example 8 | ITO | NPB | CBP(host) + 6.5% compound5 (dopant) | BCP | Alq | MgIn | 21,000 | 11.4 | 583 | 0.53, 0.46 |
| Inventive Example 9 | ITO | NPB | CBP(host) + 6.5% compound6 (dopant) | BCP | Alq | MgIn | 11,200 | 4.8 | 630 | 0.65, 0.34 |
| Inventive Example 10 | ITO | NPB | CBP(host) + 6.5% compound7 (dopant) | BCP | Alq | MgIn | 11,000 | 4.7 | 625 | 0.64, 0.35 |
| Inventive Example 11 | ITO | NPB | CBP(host) + 6.5% compound8 (dopant) | BCP | Alq | MgIn | 11,000 | 4.7 | 630 | 0.65, 0.34 |
| Inventive Example 12 | ITO | NPB | CBP(host) + 6.5% compound9 (dopant) | BCP | Alq | MgIn | 10,000 | 4.3 | 623 | 0.64, 0.35 |
| Inventive Example 13 | ITO | NPB | CBP(host) + 6.5% compound10 (dopant) | BCP | Alq | MgIn | 23,000 | 12.3 | 585 | 0.53, 0.46 |
| Inventive Example 14 | ITO | NPB | CBP(host) + 13% compound3 (dopant) | BCP | Alq | MgIn | 43,000 | 18.2 | 602 | 0.58, 0.42 |
| Inventive Example 15 | ITO | NPB | CBP(host) + 20% compound3 (dopant) | BCP | Alq | MgIn | 17,000 | 8 | 605 | 0.58, 0.42 |
| Inventive Example 16 | ITO | NPB | CBP(host) + 3% compound3 (dopant) | BCP | Alq | MgIn | 20,100 | 10.2 | 574 | 0.53, 0.46 |

From the results shown in Table 1, it was apparent that the use of the compounds 1 to 10, which are the triplet excited materials, as the red-orange luminescent dopants of the luminescent layers realized the red-orange light emission with high luminance at excellent luminous efficiency in the organic EL devices.

Inventive Examples 14 to 16

In the inventive examples 14 to 16, such organic EL devices were employed that each has the same structure as that of the organic EL device in the inventive example 1 except that the above compound 3 was used as the dopants of the luminescent layers. The concentrations of the respective compounds 3 used as the dopants were set to 13%, 20%, 3%, respectively, in the organic EL devices of the inventive examples 14 to 16. The organic EL devices of the inventive examples 14 to 16 were manufactured by the same method as that applied to the organic EL device of the inventive example 1.

The luminescent characteristics of the above organic EL devices were measured by the same method as that applied to the inventive example 1. The above Table 1 shows the results of measurement of the materials and the luminescent characteristics of the organic EL devices in the inventive examples 14 to 16.

According to the inventive example 14, when the concentration of the compound 3 as the dopant was 13%, the maximal luminance was 43,000 cd/m$^2$ and the luminous efficiency was 18.2 cd/A. According to the inventive example 6, when the concentration of the compound 3 as the dopant was 6.5%, the maximal luminance was 29,500 cd/m$^2$ and the luminous efficiency was 14.2 cd/A. According to the inventive example 16, when the concentration of the compound 3 as the dopant was 3%, the maximal luminance was 20,100 cd/m$^2$ and the luminous efficiency was 10.2 cd/A. According to the inventive example 15, when the concentration of the compound 3 as the dopant was 20%, the maximal luminance was 17,000 cd/m$^2$ and the luminous efficiency was 8 cd/A. From the results of the inventive examples 6, 14 to 16, it was apparent that excellent luminous efficiency was realized when the concentration of the compound 3 was from 3% to 20%.

Inventive Example 17

In the inventive example 17, an organic iridium compound was employed as a host material for the luminescent layer. In this example, an organic EL device having the same structure as that of the organic EL device in the inventive example 1 was used except that the luminescent layer contains Ir(Phq)$_3$ as a host material and contains 6.5 wt % of the compound 8 represented by the above formula (C8) as a luminescent dopant. The organic EL device of the inventive example 17 was manufactured by the same method as that of the organic EL device of the inventive example 1.

The luminescent characteristics of the above organic EL device was measured by the same method as that applied in the inventive example 1. As a result, red light emission with a peak at a 621 nm wavelength was obtained in this organic EL device. The obtained red light exhibited the relation x=0.63 and y=0.36 at the CIE chromaticity coordinate. The maximal luminance of this organic EL device was 9800 cd/m$^2$, and its luminous efficiency at this time was 4.1 cd/A.

As has been described above, it was apparent from the above inventive example 17 that red-orange light emission with high luminance was realized at excellent luminous efficiency in the organic EL device by use of Ir(Phq)$_3$1 which is the triplet excited material as the host material of the luminescent layer.

Inventive Example 18

In the inventive example 18, an organic iridium compound was employed as a hole transport material. In this example, such an organic El device was used that a hole injection electrode made of ITO, a hole transport layer of 30 nm made of Ir(Phq)$_3$, a luminescent layer of 50 nm made of Alq, and an electron injection electrode made of a MgIn alloy were stacked in turn on a glass substrate.

The luminescent characteristics of the above organic EL device was measured by the same method as applied in the inventive example 1. As a result, green light emission with a peak at a 530 nm wavelength was obtained in this organic EL device. The obtained green light exhibited the relation x=0.37 and y=0.52 at the CIE chromaticity coordinate. The maximal luminance of the device in this case was 3100 cd/m$^2$, and its luminous efficiency at this time was 1.5 cd/A.

As has been described above, it was apparent from the inventive example 18 that green light emission with high luminance was realized at excellent luminous efficiency in the organic EL device by use of Ir(Phq)$_3$, which is the triplet excited material as the hole transport material.

Inventive example 19

In the inventive example 19, an organic iridium compound was used as an electron transport material. In this example, such an organic EL device was employed that a hole injection electrode made of ITO, a luminescent layer of 50 nm, an electron transport layer of 30 nm made of Ir(Phq)$_3$, and an electron injection electrode made of a MgIn alloy are stacked in turn on a glass substrate. The luminescent layer contains NPB as a host material and contains as a luminescent dopant 5 wt % of rubrene having a molecular structure represented by a formula (16) below.

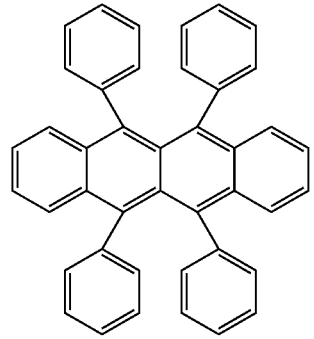

(16)

The luminescent characteristics of the above organic EL device was measured by the same method as applied in the inventive example 1. As a result, yellow light emission with a peak at a 560 nm wavelength was obtained in this organic EL device. The obtained yellow light exhibited the relation x=0.47 and y=0.51 at the CIE coordinate. The maximal luminance of the device in this case was 2800 cd/m$^2$, and its luminous efficiency at this time was 1.3 cd/A.

As has been described above, it was apparent from the above inventive example 19 that yellow light emission with high luminance was realized at excellent luminous efficiency in the organic EL device by use of Ir(Phq)$_3$, which is the triplet excited material as the electron transport material.

The invention claimed is:

1. A luminescent material having a molecular structure represented by formula (C5) below:

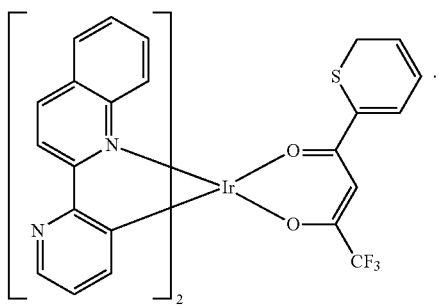

2. An organic electroluminescent device, comprising:
a hole injection electrode;
an electron injection electrode; and
a luminescent layer provided between said hole injection electrode and said electron injection electrode, wherein said luminescent layer includes a compound composed of iridium and a quinoline derivative, wherein said compound composed of iridium and a quinoline derivative has a molecular structure represented by a formula (C5) shown below:

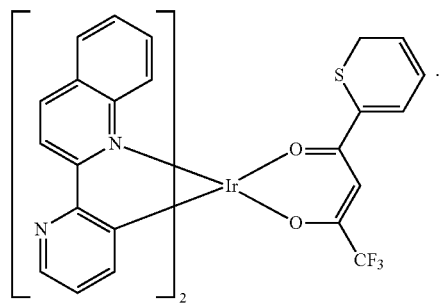

* * * * *